United States Patent [19]

Hallock et al.

[11] Patent Number: 4,847,399

[45] Date of Patent: Jul. 11, 1989

[54] PROCESS FOR PREPARING OR PURIFYING GROUP III-A ORGANOMETALLIC COMPOUNDS

[75] Inventors: Robert B. Hallock, Newburyport; Stephen J. Manzik, Plaiston, N.H.; Thomas Mitchell, Millis, Mass.; Benjamin C. Hui, Peabody, both of Mass.

[73] Assignee: Morton Thiokol, Inc., Chicago, Ill.

[21] Appl. No.: 6,392

[22] Filed: Jan. 23, 1987

[51] Int. Cl.$^4$ .......................... C07F 5/00; C07F 5/06
[52] U.S. Cl. ...................................... 556/1; 556/187; 568/1; 568/7; 423/130
[58] Field of Search .................. 556/1, 187, 188, 189; 568/1, 7; 423/130

[56] References Cited

U.S. PATENT DOCUMENTS 4,797,500  1/1989  Kadukura ............................. 556/1

FOREIGN PATENT DOCUMENTS 2183651  6/1987  United Kingdom .

Primary Examiner—Michael L. Shippen
Attorney, Agent, or Firm—George Wheeler; Gerald K. White

[57] ABSTRACT

Methods for forming or purifying organometallic compounds of elements of Group III-A of the Periodic Table. An intermediate compound is formed which is an adduct of the desired organometallic compound and a Group I-A or Group II-A compound. The adduct is nonvolatile, so volatile impurities are removed from the adduct by distillation. The adduct is decomposed to release the volatile organometallic compound, which is then distilled away from the nonvolatile remainder of the adduct. The method can be used to produce organometallic compounds which are substantially free of volatile metallic compounds and complexed solvents. A method of separating volatile Group II-B impurities from volatile Group III-A compounds is also disclosed.

12 Claims, No Drawings

PROCESS FOR PREPARING OR PURIFYING GROUP III-A ORGANOMETALLIC COMPOUNDS

TECHNICAL FIELD

This specification relates to the preparation or purification of volatile organometallic compounds having the structure:

$$M^1R_a$$

wherein $M^1$ is an element of Group III-A of the Periodic Table; each R is independently selected from hydrogen, hydrocarbyl, and combinations thereof; and "a" is an integer determined by the valence of $M^1$, typically three.

BACKGROUND ART

Organometallic compounds of Group III-A elements of the Periodic Table, and particularly the lower alkyl compounds of these elements, are extensively used to deposit compounds of their constituent elements on substrates by chemical vapor deposition. For example, gallium arsenide semiconductor layers have been deposited on substrates by combining the vapors of a gallium source such as trimethylgallium with an arsenic source such as arsine at an elevated temperature in the presence of a suitable substrate. Similar processes are used to form other III-V compounds, for example, indium phosphide from trimethylindium and phosphine. The Group III-A compounds are preferably supplied as liquids from a bubbler, where they are evaporated in a stream of carrier gas for delivery to the deposition chamber. For this mode of delivery, therefore, it is desirable that the organometallic sources of Group III-A compounds be volatile and be liquid at some temperature between roughly 0° Celsius and 150° Celsius.

The Group III-A source compounds for chemical vapor deposition, particularly for formation of III-V compounds, are required to be exceptionally pure to produce coatings of the grade necessary for electronic and other demanding applications. When the compounds are delivered as liquids from a bubbler, nonvolatile impurities are not especially significant because they are not evaporated in the bubbler apparatus, and thus are not transported to the substrate. Volatile impurities, however, are carried into the deposition chamber, and thus must be minimized in chemical vapor deposition source compounds. Even a few parts per million of volatile impurities can have a significant effect on the properties of the deposited film. See for example Jones, et al., "Analysis of High Purity Metalorganics by ICP Emission Spectrometry," *Journal of Crystal Growth*, Vol. 77, pp. 47-54 (1986), especially page 47, column 1. (This article is not admitted to be competent prior art.)

One aggravating factor is that many interfering solvents and organometallic compounds are volatile, and thus are difficult to separate from the volatile Group III-A sources by physical means. For example, the Jones, et al. article cited above indicates the difficulty of removing volatile microimpurities from Group III-A alkyl compounds by distillation. One specific example of organic contamination of a Group III-A alkyl compound is the presence of complexed ether in trialkylindium compounds, which are prepared in an ether solvent. The ether is tightly complexed and thus inseparable. Prior attempts to separate the complexed ether have involved high temperature, repeated distillations which waste most of the desired product and do not remove all the complexed ether. A specific example of organometallic contamination is the presence of alkyl silanes such as tetramethyl silane or Group II-B alkyls such as dimethylzinc.

The previously cited Jones article teaches that Group III-A organometallic compounds can be separated from organometallic and organic impurities by forming a nonvolatile adduct of the desired organometallic compound with 1,2-bis(diphenylphosphino) ethane. Materials which do not form such adducts, including ether, other organic impurities, and organometallic compounds of tin, silicon, zinc, etc. can then be evaporated and removed, since they are volatile and the adduct is not. The adduct is decomposed to release the desired volatile organometallic compound. The desired compound is then distilled away from the nonvolatile 1,2-bis (diphenylphosphino) ethane and recovered.

One significant problem with the Jones, et al. process is that the adduct must be decomposed by heating it. If the adduct decomposition temperature is high, it might approach or exceed the decomposition temperature of the desired compound. A second problem is that the Jones et al. adducting agent forms adducts with volatile organometallic compounds of elements other than Group III-A elements. These interfering compounds will be released when the adduct is decomposed unless their adducts decompose at a substantially higher temperature than the adducts of the desired organometallic compound. The Jones et al. process thus will not separate all the undesirable impurities.

Various commercial Group III-A alkyls are sold as containing less than about one part per million of impurities; such compounds are often referred to as having "six nines" or "six N" purity, indicating that they are at least 99.9999% pure. Stated another way, they are said to contain less than one part per million (ppm) of impurities. However, the common commercial standard of purity is the quantity of nonvolatile constituents present in the material. Since nonvolatile impurities are of less concern than volatile impurities, and since volatile impurities have not generally been measured, the claimed degree of purity of these compounds has not directly related to their utility for chemical vapor deposition of films.

Volatile impurities (other than solvents) can be determined using inductively coupled plasma atomic emission spectroscopy analysis, taking special precautions to retain volatile impurities in the sample during analysis. (See U.S. Pat. No. 4,688,935, issued Aug. 25, 1987 Barnes et al. and hereby incorporated herein by reference.) Volatile impurities (including solvents) are also detectable by mass spectroscopy, again providing that the impurities remain in the sample during analysis. Such analysis has demonstrated that commercial materials have not been of optimum purity. It is believed to be common for materials having "six nines" purity with respect to nonvolatile constituents to have "five nines" or less purity with respect to volatile constituents such as silicon alkyls and (for gallium compounds) zinc alkyls.

DEFINITIONS

As used in this specification:

The elements of Group III-A of the Periodic Table, referred to herein as $M^1$, are boron, aluminum, gallium, indium, and thallium, of which aluminum, gallium, and indium are commonly preferred for making III-V compounds.

The elements of Group I-A and Group II-A of the Periodic Table, referred to herein as $M^2$, are hydrogen, lithium, sodium, potassium, rubidium, cesium, francium, beryllium, magnesium, calcium, strontium, barium, and radium. Of these, lithium, sodium, potassium and magnesium are preferred, and lithium is most preferred. Ammonium is also within the definition of $M^2$.

The elements of Group II-B of the Periodic Table are zinc, cadmium and mercury. These are referred to herein as $M^3$.

The elements of Group I-A of the Periodic Table are sometimes referred to herein as $M^4$ to distinguish them from elements of Group II-A of the Periodic Table.

"Hydrocarbyl" is broadly defined herein as any organic radical which forms an organometallic compound with Group III-A metals. The preferred hydrocarbyl species are alkyl groups, especially lower alkyl groups (defined as those having from one to four carbon atoms). Specifically, all isomers of methyl, ethyl, propyl, and butyl moieties are contemplated hydrocarbyl species. Other, exemplary hydrocarbyl moieties are saturated or unsaturated cycloalkyl, preferably having from about 5 to about 12 carbon atoms, most preferably cyclopentadienyl; aryl, preferably phenyl or phenyl substituted with one or more lower alkyl moieties; and any of the above substituted by nitrogen, oxygen, or other heteroatoms. "R" as defined herein is selected from hydrocarbyl and hydrogen.

"a" is an integer determined by the valence of $M^1$, and is typically three. "b" is an integer determined by the valence of $M^2$, and is typically one if $M^2$ is selected from Group I-A and two if $M^2$ is selected from Group II-A of the Periodic Table.

"X" as used herein means any suitable anion, including (but not limited to) halogen, carboxylate (for example, acetate), and nitrate, preferably halogen and most preferably chloride due to the commercial availability of pure, relatively inexpensive chlorides of Group III-A compounds.

"Distillation" is broadly defined to include all processes in which components of a mixture are separated by selectively evaporating (which includes subliming) one or more of them and transporting the vapors away. Distillation thus includes processes in which the vapors are not collected and condensed.

A "microimpurity" as used herein means a detectable impurity present as less than about 20 ppm of the desired compound.

"Substantially free of" means containing less than one part per million of the specified impurity.

"Parts per million", abbreviated ppm, means parts of impurity by weight per million parts of the impure compound by weight.

A mixture of two compounds is said to be "separable" if one can be made substantially free of the other by a physical separation such as distillation, without carrying out a chemical reaction involving either of the separable compounds. Compounds are said to be "inseparable" if not separable according to the preceding test.

"Solvent" is broadly defined to include the liquid medium of a suspension or slurry, as well as a component of a true solution. All solvents and other materials described herein are anhydrous.

A "complexing solvent" is one which is inseparable from the target compound because it forms a complex which is resistant to decomposition by distillation. All other solvents are "noncomplexing" solvents. The most important complexing solvent in the present context is ether. Particular examples of noncomplexing solvents for the present purpose are any solvents which do not contain electron donor atoms such as oxygen, nitrogen, or sulfur. Acceptable noncomplexing solvents include aliphatic hydrocarbons such as pentane or hexane, chlorinated aliphatic solvents such as chloroform or carbon tetrachloride, aromatic solvents such as benzene and naphthalene, aliphatic-substituted aromatic solvents such as toluene or xylene, heterosubstituted aromatic solvents such as chlorobenzene, and others.

"Ether" is defined herein to mean diethyl ether in working examples. Elsewhere, "ether" includes other ethers (including cyclic ethers such as tetrahydrofuran) which are complexing solvents.

"Volatile" compounds are those having a room temperature vapor pressure greater than or equal to 30 millitorrs. "Nonvolatile" materials are those having a room temperature vapor pressure of less than 30 millitorrs.

"Preparing" means either the original preparation of a compound or the purification of a previously prepared compound by forming, separating, and then decomposing an adduct of that compound.

SUMMARY OF THE INVENTION

One object of the present invention is to prepare Group III-A organometallic compounds having less total volatile organometallic impurities than before—preferably less than one ppm.

A first aspect of the invention is a process for preparing compounds having the formula:

$$M^1R_a$$

As the first step of the process, a nonvolatile intermediate compound (adduct) is prepared which has the following structure:

$$[M^1R_{(a+1)}]^-{}_b[M^2]^{+b}$$

The adduct is formed in the presence of volatile impurities which are to be removed, and which are inseparable from the target compound once it is formed. The volatile impurities present with the adduct, including any complexed ether, are then removed by evaporating the volatile impurities and separating their vapors from the intermediate compound. Next, the adduct is decomposed to form the target compound. The decomposition is preferably effected according to the following reaction:

$$c[M^1R_{(a+1)}]^-{}_b[M^2]^{+b} + dM^1X_a \rightarrow eM^1R_a + fM^2X_b$$

wherein X is any suitable anion, preferably halogen, and c, d, e and f are integers which balance the equation.

Finally, a postdistillation step is used to separate the target compound from residual organometallic (especially silicon alkyl) impurities.

Surprisingly, the present inventors have found that the residual silicon alkyls and other impurities can be removed by distillation, contrary to the teaching of Jones et al. that distillation cannot be used to remove microimpurities of volatile organometallic materials from volatile organometallic target compounds.

One advantage of the decomposition reaction in this process is that the yield of the target compound is increased because the decomposition reagent is a compound of the metal in the target compound. A second advantage of employing this reaction is that the decomposition products are the volatile target compound and a nonvolatile compound of a Group I-A or Group II-A metal. The volatile product can easily be separated by a distillation process employing the different volatility of the two products of the decomposition reaction. A third advantage of this process is that it does not rely primarily on heat to break down the adduct and release the target compound. Unlike prior adduct processes, the adduct here can be broken down at room temperature or an even lower temperature in most instances.

Fourth, use of a compound of $M^1$ as the decomposition reagent avoids introducing another metal which can remain as a contaminant.

In the above process, the intermediate compound can be formed in a variety of ways. Several exemplary syntheses are provided later in this specification.

A second aspect of the invention is a process for separating volatile, organometallic Group II-B microimpurities from volatile, organometallic Group III-A compounds. One utility for this process is as an initial step in the first process above. The first step of the separation process is conducted by providing a volatile Group III-A compound containing as a microimpurity one or more volatile Group II-B compounds. The Group III-A compound and microimpurities respectively have the structures:

$$M^1R_a$$

and $$M^3R_2$$

This mixture is reacted with an amount of an adducting agent which is less than the stoichiometric amount with respect to the compound of $M^1$. The formation of adducts of compounds of $M^1$ is favored slightly over the formation of adducts of $M^3$ compounds. Thus, the result will be selective formation of an adduct of the following formula:

$$[M^1R_{(a+1)}]_b^-[M^2]^{+b}$$

A small portion of $M^1R_2$ and essentially all of the microimpurity $M^3R_a$ remain as an unreacted residue. Since both these starting materials are volatile and the adduct is nonvolatile, the starting materials can be removed from the adduct by a distillation process. The adduct is then decomposed as before and the target compound, $M^1R_a$, can be removed from the nonvolatile decomposition product by distillation.

DESCRIPTION OF THE PREFERRED EMBODIMENTS

The first step is formation of a nonvolatile intermediate compound having the formula:

$$[M^1R_{(a+1)}]_b^-[M^2]^{+b}$$

This adduct can be formed in a variety of ways.

In one embodiment, the starting material is an impure version of the target compound. In this case, the formation and eventual decomposition of the adduct is a purification process. The intermediate compound can be formed from the impure target compound by reacting the latter compound with an organometallic compound of $M^2$, according to the following reaction:

$$bM^1R_a + M^2R_b \rightarrow [M^1R_{(a+1)}]_b^-[M^2]^{+b}$$

In this reaction, the preferred adducting compound, $M^2R_b$, is an alkyl lithium, preferably methyllithium, which will form a complex according to the previous reaction only with volatile organometallic compounds of Group II-B and III-A. It will not react with volatile compounds of other elements to produce a nonvolatile adduct. Thus, volatile compounds of other elements can be removed from the adduct easily by distillation, while nonvolatile compounds of other elements will remain behind when the adduct is decomposed and the volatile target compound is separated by distillation.

Another advantage of these adducting reagents is that, in the event any reactant is complexed with ether, the ether is more loosely complexed in the intermediate compound, and thus can be removed by heating the adduct gently. Even if ether is complexed, for the purposes of the present specification, it is considered to be a separable impurity to the extent that it can be removed from the intermediate compound by distillation.

A second way to form the intermediate compound from an impure starting material the same as the target compound is to react the starting material with metallic $M^4$, according to the following reaction:

$$cM^4 + dM^1R_a \rightarrow c[M^1R_{(a+1)}]_b^-[M^4]^{+b} + eM^1$$

wherein c, d, and e are integers having values necessary to balance the equation and $M^4$ is selected from Group I-A and excludes Group II-A metals. This method usually is less preferred than the first reaction indicated above for forming the intermediate compound. One of the nonvolatile products is the free metal of the target compound, so some of the target compound will not be reconstituted at the end of the process. This problem can be alleviated by recycling the free metal to reform a metal alkyl or other compound. If this process is employed, $M^4$ is preferably lithium or sodium.

A third method of forming the intermediate compound is by carrying out the following reaction:

$$b\,M^1X_a + (a + 1)\,M^2R_b \xrightarrow{\text{ether}} [M^1R_{(a+1)}]_b^-[M^2]^{+b} + a\,M^2X_b$$

In this process, the preferred metal alkyl is again an alkyl lithium, most preferably methyllithium. The preferred $M^1X_a$ reactant is the chloride of the metal of the target compound. An advantage of this reaction is that the generally nonpyrophoric adduct is formed from a nonpyrophoric reactant, $M^1X_a$, without first forming the generally pyrophoric compound $M^1R_a$. This process is a method for forming a pure compound, rather than a purification.

Having formed the intermediate compound, the next step is to isolate it from all volatile impurities by distilling them away. This step will remove volatile starting materials which do not form a nonvolatile adduct. It will also remove noncomplexing solvents, since there is no particular impediment to their evaporation and removal. Less evident is that complexing solvents, in particular ether, are also removed by this step, since the complex of ether with the adduct is not nearly as difficult to separate as the complex of ether with the organometallic target compound. This is particularly true in the event the target compound is an indium compound, which is typically formed only in an ether solvent, and which is inseparable from the ether. The ether can be thought to be complexed loosely with the $[M^2]^{+b}$ ion of the adduct, rather than with the $[M^1R_{(a+1)}]^-$ ion with which it is associated before the adduct is formed.

The separation of volatile impurities and starting materials can be assisted by heating the reaction product, by exerting a partial or complete vacuum in the chamber in which the adduct is held, or by a combination of these methods.

The separable volatile impurities having been removed, the adduct is decomposed to release the target compound, which is volatile, from the rest of the adduct, which is nonvolatile.

A less preferred but sometimes acceptable way of decomposing the intermediate compound is by heating it, as has been done in other adducting methods described above in the Background Art section of this specification. If this is done, the disadvantages of the other adducting processes can also be expected.

A preferred way to decompose the adduct is to react it with a reagent. The preferred reagent, $M^1X_a$, can also increase the yield, if it is a compound of the metal of the target compound. The preferred reaction scheme for decomposing the intermediate compound is as follows:

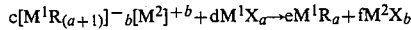

wherein c, d, e, and f are the integers necessary to balance the equation.

If the adduct is formed by adding $M^1X_a$, it also can be decomposed by adding an additional quantity of the same reagent. Thus, if this forming and decomposing scheme is employed, it is important not to add an excess quantity of the adduct forming reagent at first, thereby avoiding premature regeneration of the target compound. However, this precaution is not critical; if a small proportion of the target compound is formed when the adduct is formed it will be removed during the step in which volatile impurities are removed.

Finally, microimpurities are removed by distillation following the decomposition step. The distillation pot is heated just enough to melt the target compound and distill away the microimpurity from the target compound. A surprising aspect of the postdistillation step is that it can be used to render the target compound essentially free of microimpurities, even though larger amounts of impurities cannot be directly removed by distillation, and must be removed by the adduct forming and decomposing process.

A second aspect of the present invention is a process for separating Group II-B impurities from Group III-A volatile, organometallic compounds. This process can be used as a precursor to practicing one of the previously described processes, or to separate these organometallic compounds for any other purpose.

The first step is to provide a mixture of a major proportion of a Group III-A compound and a volatile Group II-B organometallic microimpurity. The target compound and microimpurity respectively have the structures:

and

Each constituent of this mixture is volatile, and thus the constituents are difficult to separate by a physical process so the target compound is substantially free of the microimpurity. This mixture is reacted with a less than stoichiometric amount of an adducting reagent. The adducting reagent can be any reactant or combination of reactants which has previously been described as being capable of forming the previously described intermediate compound.

A critical aspect of this process is that compounds of $M^1$ form a complex more easily than compounds of $M^3$ do when both are present. If less than a stoichiometric amount of the adducting agent is used, only the compounds of $M^1$ which are present will form an adduct.

Next, volatile constituents are separated from the adduct as before. Since the compounds of $M^3$ are not able to form a complex and are volatile, they are removed by the separation process, as are other volatile impurities. The target compound of $M^1$ is then reformed by decomposing the adduct as previously described. The product of decomposition of the adduct is an organometallic compound of $M^1$, substantially free of compounds of $M^3$.

EXAMPLES

The following examples are provided to illustrate various aspects of the present invention. The scope of the invention, however, is defined by the claims which conclude this specification. All manipulations described in the examples are performed in vacuo or under an inert atmosphere of nitrogen or argon gas. All reactants and products specified herein are anhydrous.

EXAMPLE 1

Preparation of InMe₃

Part 1—Preparation of LiInMe₄

In this part the following reaction was carried out ("Me" is methyl):

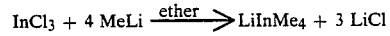

In a glove bag, 1500 grams (6.78 moles) of InCl₃ were weighed into a 12 liter, 3 neck flask which was previously evacuated and backfilled with nitrogen. The 12 liter flask was placed in a heating mantle and supported on a large jackstand. The 12 liter reaction flask was then equipped with a 1 liter addition funnel, mechanical stirrer, and an 18 inch (46 cm) Vigreux column connected to a 5 liter, 3 neck receiver by a Claisen head. ("Vigreux" and "Claisen" are not believed to be trademarks.) The 5 liter receiver was connected to a nitrogen bubbler. A source of methyllithium (1.5 molar, low halide, in diethyl ether) was connected via stainless steel tubing to the 1 liter addition funnel.

The drip tip of the addition funnel extended below the level of the greased joint, since MeLi is reactive towards halocarbon grease.

About 2 liters of diethyl ether were pressure siphoned into the 12 liter reaction flask to make a stirrable slurry with the InCl₃.

The 5 liter receiver and dry ice condenser were cooled with a mixture of isopropanol (IPA) and dry ice, and the addition of MeLi was begun. The reaction was run at reflux and ether was distilled up the Vigreaux column and collected in the 5 liter receiver. It was not necessary to heat the reaction flask, as the heat of reaction was sufficient to maintain reflux.

The addition of MeLi was continued until 4.4 moles MeLi per mole of InCl$_3$ had been added. The concentration of the MeLi was determined by titrating several 10 ml. aliquots with standard acid solution (0.1N hydrochloric acid). When the 12 liter reaction flask became full, it was necessary to stop the addition of MeLi and distill off ether by heating the reaction mixture to reflux using a heating mantle. The receiver was emptied several times during the process by siphoning out the distilled ether. The total volume of MeLi solution added was about 20 liters (4.4 moles of MeLi per mole of InCl$_3$).

After the MeLi was added to the 12 liter reaction flask, the addition funnel was removed and replaced with a nitrogen inlet with a shutoff valve. The reaction flask was heated with the heating mantle to continue distilling off ether until the volume of the reaction mixture was below 5 liters. At this point, stirring was discontinued and the reaction mixture was allowed to settle overnight.

The Vigreux column, Claisen head, and receiver were removed from the reaction flask. The reaction mixture consisted of a white precipitate (LiCl and a polymer of methyllithium) which settled out beneath an orange solution.

EXAMPLE 1

Part 2—Vacuum Drying of LiInMe$_4$

A 5 liter stainless steel kettlehead drying flask with a 3 neck glass top (o-ring seal) was equipped with a nitrogen inlet having a shutoff valve, and with a stirring bar. This drying flask was connected by a U-tube to a 5 liter, 3 neck receiver with a dry ice condenser. The condenser was connected by vacuum tubing to a valve, a liquid nitrogen trap, a vacuum gauge, a second valve, and a vacuum pump, arranged in that order. The stainless steel drying flask was heated in an oil bath and supported on a combined heating/stirring plate and jackstand. The apparatus was evacuated and backfilled with nitrogen several times.

The 12 liter reaction flask containing the reaction mixture of Part 1 was elevated and the orange solution was siphoned through nonreactive flexible tubing into the 5 liter stainless steel drying flask, taking care not to siphon over any of the precipitate of LiCl and excess polymerized MeLi.

After the majority of the orange solution of LiInMe$_4$ (the intermediate compound) in ether had been removed from the 12 liter reaction flask, 2-3 liters of ether were pressure siphoned into the 12 liter flask to wash the precipitate. The mixture was stirred for at least one hour and then allowed to settle overnight.

Vacuum was slowly applied to the 5 liter drying flask to strip off ether. The oil bath temperature was maintained at about 30° C. to replace the heat lost due to the evaporation of the ether. The receiver and condenser were cooled with a dry ice/IPA slurry. The distilled ether was periodically siphoned out of the receiver during this step.

After the volume of material in the 5 liter drying flask was reduced to less than 2 liters, the light yellow supernatant wash from the 12 liter reaction flask was siphoned into the 5 liter drying flask, again taking care to leave the precipitate behind.

Vacuum was again slowly applied to the drying setup and the oil bath temperature was slowly raised. This process was continued until full vacuum was reached and the oil bath temperature reached 120° C. The LiInMe$_4$ was dried for several hours at full vacuum and 120° C. at this point. The apparatus was then backfilled through the nitrogen inlet shutoff valve on the 5 liter flask and allowed to cool to room temperature.

The U-tube and receiver were removed from the 5 liter stainless steel drying flask. The stainless steel flask was brought into a glove bag along with a stainless steel mortar and pestle, a funnel, a spatula and a tared 5 liter, 3 neck glass flask equipped with a mechanical stirrer and two nitrogen inlets with shutoff valves. The glass top was removed from the stainless steel drying flask and the tan, solid LiInMe$_4$ adduct was ground to a fine powder using the mortar and pestle. After grinding the adduct, it was transferred into the 5 liter glass flask.

The flask containing the LiInMe$_4$ was placed in an oil bath and connected directly to a liquid nitrogen trap with vacuum tubing. Full vacuum was applied to the flask and the oil bath temperature was raised to 120° C. The LiInMe$_4$ was dried under these conditions for more than two hours, then backfilled through the 5 liter flask and allowed to cool to room temperature. The weight of dry LiInMe$_4$ was then determined to calculate the weight of InCl$_3$ required for the next reaction.

EXAMPLE 1

Part 3—Decomposition of LiInMe$_4$

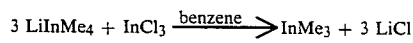

$$3\ \text{LiInMe}_4 + \text{InCl}_3 \xrightarrow{\text{benzene}} \text{InMe}_3 + 3\ \text{LiCl}$$

The dry LiInMe$_4$ produced in Part 2 was weighed and the weight of InCl$_3$ necessary for the final reaction was calculated.

In a glove bag, the stoichiometric amount of InCl$_3$ was weighed into a 2 liter, one-neck flask. This flask was equipped with a piece of large diameter tubing about 2 feet long with a male joint and small flask at the end. About 2 liters of benzene were siphoned into the 5 liter flask containing the LiInMe$_4$ so that a stirrable slurry was obtained. The 5 liter flask was placed in an oil bath and equipped with a Y-tube to fit a dry ice condenser and thermowell on one neck of the 5 liter flask. The small "dummy" flask was removed from the end of the tube connected to the InCl$_3$ flask and the male joint on the end of the tube was connected to the 5 liter flask. The InCl$_3$ was transferred a little at a time into the LiInMe$_4$/benzene slurry. The addition rate was such that the temperature of the reaction remained below the reflux temperature of benzene (80° C.) Between additions of aliquots of InCl$_3$, the tubing was clamped shut so the InCl$_3$ would not become wet from benzene vapors and clog in the tube. The addition of InCl$_3$ required several hours.

After the addition of InCl$_3$ was complete, the reaction mixture was allowed to cool to room temperature while stirring. The InCl$_3$ addition flask and tubing were removed and replaced with a nitrogen inlet having a shutoff valve. The Y-tube, dry ice condenser and thermowell were removed.

Example 1

Part 4—Removal of Benzene and Microimpurities by Distillation

The 5 liter reaction flask of Part 3 was equipped with an 18 inch (46 cm) Vigreux column connected by a Westcott water condenser to a 3 liter receiver. ("Westcott" is not believed to be a trademark.) The receiver was cooled in an ice bath and benzene was distilled away from the reaction mixture at atmospheric pressure. The oil bath was maintained at about 110° C. and the head temperature was about 80°-83° C. After most of the benzene was distilled away, the reaction mixture appeared to thicken. The stirrer shaft was lifted a few inches, so that its paddle was suspended above the level of the molten reaction mixture, and clamped in this position while the reaction flask cooled overnight.

On the next day, the stirring shaft was removed from the 5 liter reaction flask containing a solid mixture of InMe$_3$, LiCl and benzene. A 3 liter, 3 neck flask containing a stir bar and a dry ice condenser was connected to the 5 liter flask with a U-tube. The U-tube was wrapped with heat tape. The dry ice condenser was connected by vacuum tubing to a valve, liquid nitrogen trap, pressure gauge, valve and vacuum pump (in that order).

Vacuum was applied to the system at room temperature. The receiver and condenser were kept at room temperature. Any benzene which came over was allowed to pass into the liquid nitrogen trap. When the trap began to clog with frozen benzene, the valves on both sides of the trap were closed, it was removed from the liquid nitrogen, the benzene was melted down to the bottom of the trap, then the trap was returned to the Dewar flask of liquid nitrogen. ("Dewar" is not believed to be a trademark.)

The oil bath was warmed to 30°-35° C. to keep benzene from freezing in the 5 liter flask, and the U-tube was warmed by the heat tape to prevent benzene from freezing within it. When crystals of InMe$_3$ began to collect in the receiver, the receiver and the dry ice condenser were cooled with dry ice/IPA. The oil bath temperature was brought up to 50° C. and the sublimation continued.

To sublime a kilogram of the InMe$_3$ required about nine days. Each morning the start-up procedure described above was repeated to remove traces of benzene from the InMe$_3$. After several days of sublimation, the reaction mixture was chopped up carefully with a spatula in the morning while the reaction mixture was cool. After each day of sublimation, the apparatus was backfilled through the nitrogen inlet on the 5 liter flask. The sublimation was finished when only fine, light brown, solid LiCl remained in the 5 liter flask.

EXAMPLE 1

Part 5—Resublimation and Separation of Microimpurities

The apparatus used for the first sublimation of the InMe$_3$ was disassembled, and the 3 liter flask containing the sublimed InMe$_3$ and a stirring bar was connected by a U-tube to a 1 liter receiver equipped with a small dry ice condenser. The apparatus was set up in the same way as described for the first sublimation.

The heat tape on the U-tube was warmed. While at atmospheric pressure, the 3 liter flask was heated in an oil bath to 90°-110° C. in order to completely melt the InMe$_3$. The molten InMe$_3$ was stirred with the stir bar.

The receiver and condenser were cooled with dry ice/IPA. The nitrogen inlet valve on the 3 liter flask was then closed and the pressure in the system slowly reduced until the InMe$_3$ began bubbling. The pressure reduction in the system was continued carefully until about 20-30 g of material had been collected in the receiver. At this point, the apparatus was backfilled through the 3 liter flask and allowed to cool to room temperature overnight.

The 1 liter receiver containing the forerun was replaced with a 3 liter, 3 neck flask equipped with a dry ice condenser. The sublimation was begun again, following the startup procedure described for the first sublimation. The sublimation was continued until only about 50 grams of material remained in the heated flask. The second sublimation was carried out in the same manner as the first sublimation and took about the same amount of time. As in the first sublimation, the system was brought down to full vacuum each morning with the receiver at room temperature for a short while before cooling it to −78° C. This procedure helped to remove traces of benzene from the InMe$_3$.

After the sublimation was completed, the system was backfilled and disassembled. The 3 liter flask containing the doubly sublimed InMe$_3$ was equipped with a nitrogen shutoff valve. After the InMe$_3$ warmed to room temperature overnight, the 3 liter flask was attached directly to a liquid nitrogen trap and full vacuum was applied for one hour at room temperature. The 3 liter flask was then brought into the drybox while under vacuum for storage.

The product was analyzed by inductively coupled plasma atomic emission spectroscopy, and found to contain only 1 ppm of silicon.

EXAMPLE 1

Part 6—InP Film Growth

The product of Part 5 and phosphine gas were used in an atmospheric pressure vapor phase epitaxy process to grow an indium phosphide semiconductor layer, which was then tested for electrical properties. The electron mobility of the layer (cm$^2$/V s) at 77K was 131,000, which is believed to be the highest value ever obtained and is indicative of extremely low solvent and organometallic microimpurity levels in the source compounds.

EXAMPLE 2

Removal of Zn and Si from Trimethylgallium

Part 1: Preparation of LiGaMe$_4$
The following reaction was carried out:

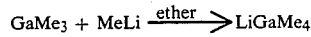

The starting trimethylgallium (TMG) was first analyzed for silicon and zinc impurities by inductively-coupled plasma atomic emission spectroscopy (ICP). An average of 42 ppm of volatile silicon alkyl compounds and roughly 5 pm of volatile zinc alkyl compounds were found. The detection limit of each of these impurities was about 0.5 ppm.

A 12 liter, stainless steel kettlehead flask was provided with a three neck glass top, an O-ring seal, a magnetic stirring bar, and a one liter addition funnel. The flask was evacuated to a pressure of 0.5 mm Hg (66 N/m$^2$). 1207 ml. (1363 grams, 11.87 moles) of TMG was added to the flask from a supply tank through a short length of hose, via the addition funnel. Then about 11 moles of MeLi (about 1.3M in ether, 8.45 liters) were added to the TMG through the course of about two days, via the addition funnel. The reaction was exothermic.

Once addition of MeLi was complete, a three liter receiver with a dry ice condenser, a liquid nitrogen trap, and a vacuum pump were connected (in that order) to the 12 liter flask. Ether was evaporated from the flask until the adduct in the flask was dry. The final pot temperature and pressure were 120° C., 0.4 mm. Hg (53 N/m²). The apparatus was then backfilled with nitrogen and the adduct was removed from the flask and ground under nitrogen. It was then dried at 110° C., 0.3 mm. Hg (40 N/m²) pressure for about one hour in similar apparatus. A small amount of unreacted TMG was isolated in the liquid nitrogen trap, confirming that a slightly less than stoichiometric proportion of MeLi was originally added. 1607 grams (11.75 moles) of LiGaMe₄ were isolated.

EXAMPLE 2

Part 2: Reformation of TMG

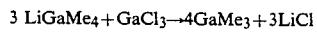

1598 grams (11.68 moles) of the product of Part 1 were weighed into a 12 liter, 3-neck glass flask. 1 gallon (3.79 liters) of toluene was siphoned into the flask and an additional 325 ml of toluene was placed in an addition funnel attached to the flask. 3.89 moles of GaCl₃ (685 grams) were melted and dissolved in the toluene in the addition funnel, and additional toluene (about 255 ml) was used to wash GaCl₃ down from the GaCl₃ ampoule and the upper part of the addition funnel. The gallium chloride/toluene solution was added to the adduct in the flask over about two hours.

EXAMPLE 2

Part 3—Crude Distillation of TMG

The 12 liter flask was equipped with a distillation column (vacuum-jacketed, silvered, packed with an efficient stainless steel packing), Claisen head, and one liter forerun receiver fitted with a dry ice condenser. The 12-liter flask was heated with an oil bath, the receiver was held at −78° C., and TMG began to distill into the receiver when the pot temperature was about 50° C. and the head temperature was about 55° C. About 50 ml of TMG were collected in the forerun. The forerun was analyzed by ICP and found to contain about 3 ppm of silicon, and no detectable zinc.

The forerun receiving vessel was replaced with a five liter receiving flask, then the main fraction of TMG was distilled at a head temperature of from 85° to 106° C. and a pot temperature of 100°–116° C. About 2.5 liters of TMG were collected.

EXAMPLE 2

Part 4—Second Distillation

A 20 plate bubble column with a partial take off head and a one liter forerun receiver were assembled on a distillation flask, and the TMG was distilled again. The pot temperature stabilized at 80° C. and the head temperature stabilized at 55° C. A 100 ml forerun was collected. The forerun was analyzed by ICP; silicon and zinc were not detectable. A larger receiver was installed and the main fraction of TMG was distilled over at a pot temperature of 81° to 109° C., with a head temperature of 55° to 56° C. Finally, a tail fraction was taken in a third receiver. The pot residue was sampled for analysis.

The analysis of the main fraction showed nondectable amounts of silicon and zinc, as did the analysis of the pot residue.

This example shows that if less than a stoichiometric amount of MeLi is reacted with TMG, volatile compounds of zinc (and any other volatile Group II-B compounds) are removed. The inventors believe the zinc does not form a complex under these conditions, and is distilled away when the adduct is dried. This example also shows that the volatile silicon alkyls in the starting material are almost completely removed due to the adduct forming and decomposing sequence followed by post-distillation.

Example 3

Preparation of LiGaMe₄ from GaCl₃

The following reaction scheme was followed:

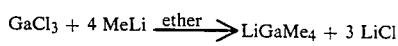

A five liter, three neck flask was set up with a one liter addition funnel, mechanical stirrer, and dry ice condenser. 250 grams (1.42 moles) of GaCl₃ were melted and poured into the flask, after temporarily removing the addition funnel. 400 ml of degassed ether was added to the flask slowly through the addition funnel to dissolve the GaCl₃; the dissolution was exothermic. Then 4.4 liters of about 1.3M MeLi (about 5.7 moles) dissolved in ether were added to the flask via a copper tube connecting the MeLi tank to the addition funnel. The reaction was exothermic, so the mixture refluxed during the addition of MeLi. During the addition, a white precipitate of lithium chloride developed. The mixture was stirred and allowed to cool to room temperature after the addition was complete. The mixture was then filtered to separate the precipitate, and the filtrate was dried. The resulting product, LiGaMe₄, was a brown solid. Volatile materials were stripped from the product by holding it at a pressure of less than 0.5 mm. Hg. (66 N/M²) and a temperature of up to 127° C. for about eight hours. The dry product was then ground and weighed: 131 grams (67% yield) of LiGaMe₄ were formed.

The LiGaMe₄ was tested for volatility by heating a small sample at the rate of 3° C. per minute, starting at 150° C. At 220° C. no signs of melting or decomposition were noted. At 289° C. it had started to decompose but had not melted.

EXAMPLE 4

Purification of AlEt₃

Part 1—Formation of NaAlEt₄

The following reaction was carried out (note: "Et" means ethyl):

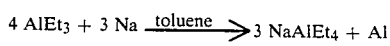

A five liter, three neck flask was evacuated and back-filled with nitrogen. In a glove bag, 5.6 moles (130 grams) of sodium metal dispersed in toluene were added to the flask. Then a magnetic stirring bar, a dry ice condenser, and a one liter addition funnel were connected to the flask, and it was placed in an oil bath. About three liters of toluene were added to the flask, then the addition funnel was charged with 540 ml (3.95 moles) of AlEt₃. The oil bath was heated to 70 to 75° C., then AlEt₃ was slowly added over about two hours. Once the exothermic reaction began, the oil bath heater was shut off. After addition was complete the flask was heated to 100° C., then cooled and allowed to stand three days. The flask was heated to 65°–70° C. with stirring, and stirring was then stopped to allow the residual Na and byproduct Al metal to settle. The supernatant liquid was decanted and pressure filtered into a five liter flask while hot to separate the free metals. The filtrate was allowed to cool, and a crystalline precipitate developed. The filtrate was cooled in a −78° C. bath to promote further precipitation, then the supernatant liquid was decanted. The toluene was stripped at 70° C. for two hours under vacuum—the final vacuum was less than one mm. Hg. (133 N/m²). The crystalline NaAlEt₄ was removed from the flask and chopped up with a spatula, then the precipitate was dried for about four hours at 70° to 75° C. and 0.5 mm Hg. (66 N/M²) pressure and ground with a mortar and pestle. 263 grams (1.58 moles) of NaAlEt₄ were isolated. Its melting point is 122° to 123° C. The literature value in *J. Gen. Chem. U.S.S.R.*, Vol. 32, p. 688 (1962) is 122° to 124° C.

EXAMPLE 4

Part 2—Regeneration of AlEt₃
The following reaction scheme wa used:

3NaAlEt₄+AlCl₃→4AlEt₃+3NaCl 65 grams of AlCl₃ (0.49 moles) was weighed into a small flask in a glove bag. A tube was attached to the flask; its outboard end had a ground glass male fitting temporarily inserted in a dummy flask. 263 grams (1.58 moles) of NaAlEt₄ was slurried in about one liter of benzene in a three liter, three neck flask. The male fitting of the tube was inserted in one neck of the three neck flask, and AlCl₃ was transferred into the three neck flask in small portions over about 30 minutes. The solid constituent of the slurry changed to a fine, light precipitate of salt.

The volatiles were distilled away from the precipitate at 60°–80° C. under vacuum for about 15 hours. The precipitate was discarded. The benzene was vacuum distilled away from AlEt₃ at a pot temperature ranging from 20° to 45° C. A second receiving flask was substituted and the AlEt₃ and some benzene were distilled over; the pot residue consisted essentially of solids. Additional benzene was then removed by holding the second receiving flask at 60° C. under vacuum (0.2 mm. Hg., 27 N/cm²) for three hours. No post-distillation was conducted.

An ICP analysis of the product, AlEt₃, slowed the presence of about 5 ppm of volatile silicon alkyls.

This example shows that an undesirable level of silicon alkyls will remain in the reaction product, even if the adduct forming and decomposing process is conducted, unless a post-distillation step is employed. This example also shows one of the alternative reactions for forming the adduct from the target compound.

EXAMPLE 5

Magnesium Adduct of TMG

The following reactions are carried out and the final product is purified analogously to Example 2:

Me₂Mg+2Me₃Ga→Mg(GaMe₄)₂

3Mg(GaMe₄)₂+2GaCl₃→8GaMe₃+3MgCl₂

The first reaction is carried out with a slight molar excess of Me₃Ga and deficiency of Me₂Mg to prevent formation of adducts of zinc impurities. An ICP analysis shows nondetectible amounts (less than 0.5 ppm each) of volatile zinc and silicon compounds.

EXAMPLE 6

Purification of Other Group III Alkyls

The following reactions are carried out and the final product is purified analogously to Example 2:

MeLi+Et₃Ga→LiGaMe$_x$Et$_y$ (The sum of x+y is 4.)

3LiGaMe$_x$Et$_y$+GaCl₃→3GaMe$_z$Et$_w$+3 LiCl (The sum of z and w is 3.)
Expressed another way, the product is a mixture of the following species:

GaMe₃

GaMe₂Et

GaMeEt₂

GaEt₃

When the above mixture is distilled away from the decomposition byproducts, it is essentially converted to a mixture of GaMe₃ and GaEt₃, which respectively boil at about 55° C. and 104° C. and thus can be separated by distillation.

A slight molar excess of Et₃Ga is used in the first step to prevent formation of adducts of zinc impurities. An ICP analysis shows the amounts of silicon and zinc in the product to be nondetectible.

We claim:
1. A process for preparing a product having the formula:

M¹R$_a$ wherein M¹ is an element of Group III-A of the Periodic Table; each R is independently selected from hydrogen, hydrocarbyl, and combinations thereof; and a is 3; said product having total volatile metal compound impurities of less than 1 ppm; comprising the steps of:

A. forming a nonvolatile intermediate compound having the formula:

{M¹R$_{(a+1)}$}⁻$_b${M²}⁺$^b$ wherein M¹ is a Group III-A element, M² is selected from elements of Groups I-A and II-A of the periodic Table and ammonium, a is three, b is selected from 1 or 2, each R is independently selected from hydrocarbyl, hydrogen and combinations thereof, and said intermediate compound includes volatile organometallic impurities, B. distilling the major production of said volatile organometallic impurities away from said intermediate compound, leaving a residue of said volatile organometallic impurities mixed with said intermediate compound, C. decomposing said intermediate compound according to the following reaction:

$$c\{M^1R_{(a+1)}\}^-{}_b\{M^2\}^{+b} + dM^1X_a \rightarrow eM^1R_a + fM^2X_b$$

wherein c, d, e, and f are integers selected to balance the equation and X is an anion; thereby providing said $M^1R_a$ mixed with said residue, and D. postdistilling said $MR_a$ mixed with said residue from the liquid state, thereby selectively distilling said residue out of said $MR_a$; whereby said product contains less than one ppm of said residue.

2. The process of claim 1, wherein M is indium.
3. The process of claim 1, wherein $M^1$ is gallium.
4. The process of claim 1, wherein $M^1$ is aluminum.
5. The process of claim 1, wherein each R is alkyl.
6. The process of claim 5, wherein $M^1R_a$ is trimethylindium.
7. The process of claim 1, wherein $M^2$ is lithium.
8. The process of claim 1, wherein X is chloride.
9. The process of claim 1, wherein the product of said process contains nondetectable amounts of silicon and zinc.
10. The process of claim 1, wherein the product of said process contains nondetectable amounts of volatile organometallic impurities.
11. The process of claim 1, wherein the product of said process is suitable for growing a semiconductor layer having an electron mobility at 77° K. of at least 131,000 cm$^2$/V.s.
12. The process of claim 1, wherein said forming step is carried out by reacting an impure starting material of formula:

$$M^1R_a$$

with a less than stoichiometric amount of an adducting reagent to preferentially form said nonvolatile intermediate compound.

* * * * *